(12) United States Patent
Hata

(10) Patent No.: US 7,419,576 B1
(45) Date of Patent: Sep. 2, 2008

(54) ANALYZING APPARATUS

(75) Inventor: Yoshiaki Hata, Ashiya (JP)

(73) Assignee: Minolta Co., Ltd., Osaka-Shi (JP)

( * ) Notice: Subject to any disclaimer, the term of this patent is extended or adjusted under 35 U.S.C. 154(b) by 1142 days.

(21) Appl. No.: 09/689,010

(22) Filed: Oct. 12, 2000

(30) Foreign Application Priority Data

Oct. 12, 1999 (JP) ............ 11-289319

(51) Int. Cl.
*G01N 27/453* (2006.01)

(52) U.S. Cl. ............ 204/603; 204/601

(58) Field of Classification Search ......... 204/450–455, 204/600–605, 547, 643; 73/61.48; 422/100, 422/82.05–82.11
See application file for complete search history.

(56) References Cited

U.S. PATENT DOCUMENTS

| | | | | |
|---|---|---|---|---|
| 4,908,112 | A | * | 3/1990 | Pace ............ 210/198.2 |
| 5,296,375 | A | * | 3/1994 | Kricka et al. ......... 435/2 |
| 5,599,503 | A | * | 2/1997 | Manz et al. ....... 422/82.05 |
| 5,776,672 | A | | 7/1998 | Hashimoto et al. ...... 435/6 |
| 5,789,167 | A | | 8/1998 | Konrad ............. 435/6 |
| 5,858,195 | A | | 1/1999 | Ramsey ........... 204/601 |
| 5,867,266 | A | * | 2/1999 | Craighead ......... 356/344 |
| 5,876,675 | A | * | 3/1999 | Kennedy ........... 422/99 |
| 5,917,606 | A | * | 6/1999 | Kaltenbach ........ 356/440 |
| 5,933,233 | A | * | 8/1999 | Gunther ........... 356/318 |
| 6,091,502 | A | * | 7/2000 | Weigl et al. ........ 356/416 |
| 6,100,541 | A | * | 8/2000 | Nagle et al. ........ 250/573 |
| 6,176,990 | B1 | * | 1/2001 | Yager et al. ........ 204/601 |
| 6,440,285 | B1 | * | 8/2002 | Fuhr ............. 204/457 |

FOREIGN PATENT DOCUMENTS

| | | |
|---|---|---|
| JP | 5-199898 | 8/1993 |
| WO | WO 96/13744 * | 5/1996 |
| WO | WO 98/28604 * | 7/1998 |

OTHER PUBLICATIONS

Swerdlow, H. et al "Three DNA Sequencing Methods Using Capillary Gel Electrophoresis and Laser-Induced Fluorescence." Anal. Chem. 63, 2835. (1991).*
"Highly efficient optical detection of surface fluorescence", Applied Optics, vol. 38, No. 4, Feb. 1999, pp. 724-732.

* cited by examiner

*Primary Examiner*—Kaj K Olsen
*Assistant Examiner*—Jeffrey T Barton
(74) *Attorney, Agent, or Firm*—Sidley Austin LLP

(57) ABSTRACT

One of the principal objects of the present invention is to realize, in a small scale and at a low cost, an analyzing apparatus that analyzes and manipulates a minute sample such as DNA. The analyzing apparatus 1 incorporates an optical system for measuring a fluorescence from a sample traveling through a minute channel 24c. Specifically, a light source that generates a light for exciting a fluorescence of the sample and a light guide that guides the light from the light source to the minute channel 24c are provided, whereby the fluorescence of the sample in the minute channel 24c is well excited. In order to observe the fluorescence of the sample, a condensing optical element 26, provided on a wall surface of the minute channel 24c, for capturing the fluorescence from the sample, and a sensor section 11 are provided, whereby the fluorescence of the sample in the minute channel 24c can be well observed.

3 Claims, 10 Drawing Sheets

A—A

F I G. 6A
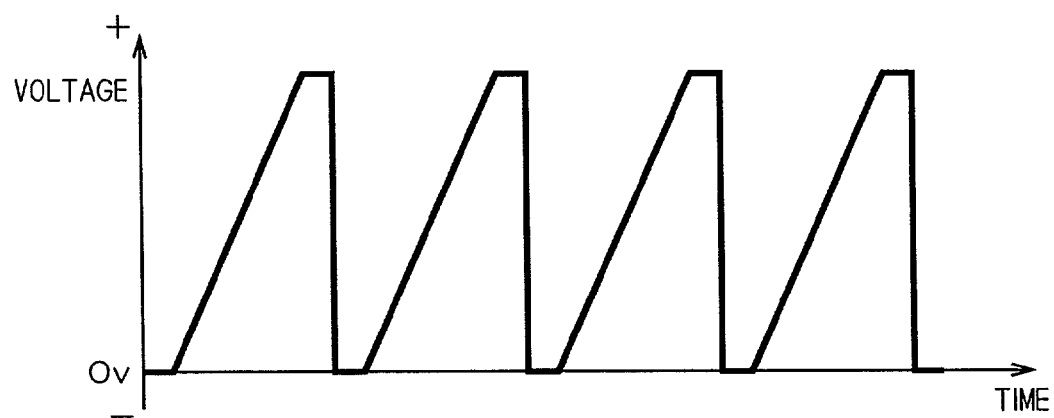
F I G. 6B
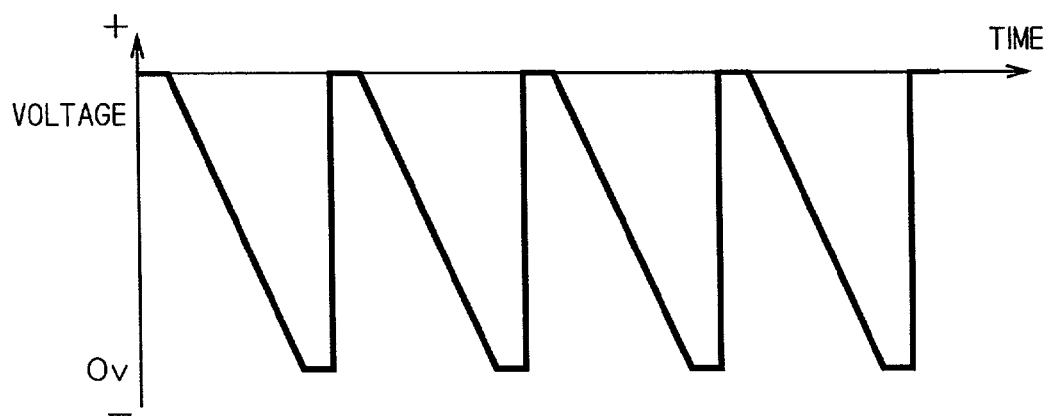

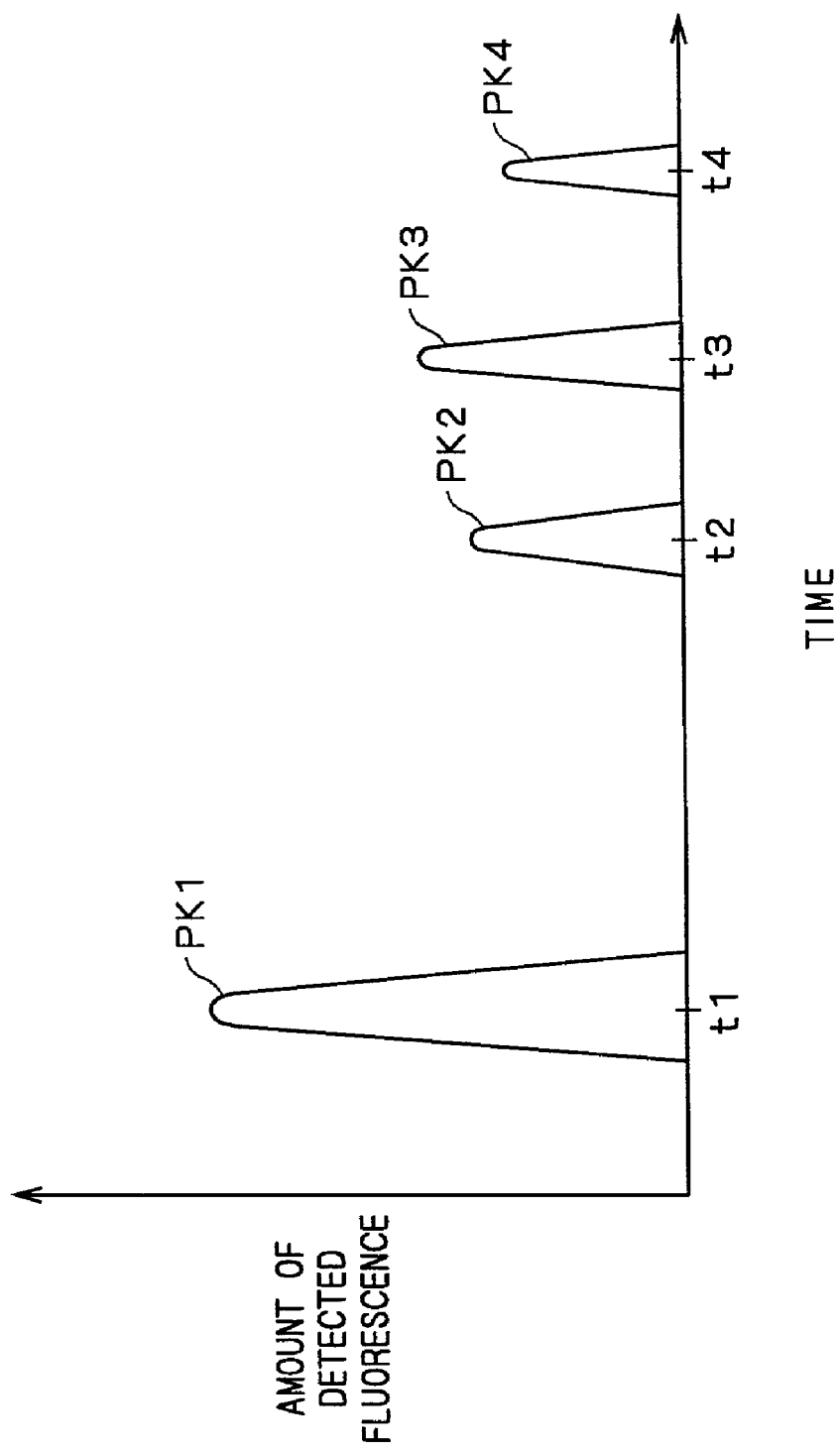

ANALYZING APPARATUS

This application is based on application No. 11-289319 filed in Japan, the contents of which are hereby incorporated by reference.

BACKGROUND OF THE INVENTION

1. Field of the Invention

The present invention relates to a technique for analyzing a biotic or biochemical minute sample, such as analysis of DNA (deoxyribonucleic acid) with the use of a technique such as MEMS (Micro Electro Mechanical Systems) or MOEMS (Micro Opto Electro Mechanical Systems).

2. Description of the Background Art

Hitherto, research is made on an apparatus (an apparatus called µTAS or the like) that measures a fluorescence of a sample (a minute substance such as DNA) in a solution flowing through a minute channel to perform various kinds of analysis. In this apparatus, the measurement of fluorescence is realized by individually assembling a light source and an optical system for projecting an excited light to a minute channel and an optical system and an optical detecting element for measuring the fluorescence around the apparatus in which the minute channel has been formed. For this reason, the assembled system as a whole performs a function of an analyzing apparatus.

An example of such an apparatus is disclosed in U.S. Pat. No. 5,858,195. This apparatus is constructed in such a manner that a complex biotic or biochemical operation (analysis or synthesis) to a sample is performed on an analyzing chip (microchip) having a size of about 5 cm×2.5 cm by an electronic control. Specifically, a plurality of water tanks for storing chemical substances and minute channels connecting the plurality of water tanks are formed on an analyzing chip, and each water tank has an individually controlled electric potential, which allows a sample to move through the minute channel among the water tanks.

As a detector that measures a sample, the characteristics and others of the sample can be detected by using, for example, those that detect optical absorption, change in refractive index, fluorescence emission, chemical emission, various Raman spectra, electrical conductivity, electrochemical current, sound wave propagation, or the like.

In performing analysis with the use of an analyzing chip, DNA is divided into fragments having different lengths with a restriction enzyme, and each fragment is allowed to move through a minute channel by electrophoresis. At a certain point in the minute channel, a light such as laser light for exciting a fluorescence is given from the outside and, when a fragment passes through that point, a prescribed fluorescent dye is excited, and the fragment is analyzed by detecting the fluorescence characteristics with a light-receiving optical system disposed on the outside.

However, the prior art technique such as mentioned above involves a problem that the size and the cost of the system as a whole increases because the devices such as the optical system that projects laser light or the like for exciting a fluorescence from the outside of the analyzing chip and the optical system for measuring the fluorescence are disposed around the analyzing chip to allow the system to function as an analyzing system. Further, a lot of labor is required for preparation and position adjustment in disposing each member around the analyzing chip in which the minute channel has been formed, thereby raising a problem that an efficient analysis cannot be carried out.

Moreover, even if an attempt is made to improve the sensitivity or the SN ratio of the fluorescence measurement by adjusting the optical system and others, it reaches a limit at a comparatively low level, and it is difficult to make a further improvement.

Furthermore, in order to repeat a stable analysis with good efficiency, it is desired to perform supply and pick-up of samples, exchange of analyzing chips, and others automatically. Also, in picking up the samples, it is desired to pick up the object samples easily without performing complex manipulations.

SUMMARY OF THE INVENTION

According to a first aspect of the present invention, a microchip includes: a channel having at least one internal surface, wherein an object to be analyzed is capable of traveling through the channel; and an optical element facing the channel to receive a light from the object, the optical element having a surface forming a part of the at least one internal surface of the channel.

Therefore, an optical system and others need not be disposed separately in an analyzing apparatus, so that the analyzing apparatus can be realized in a small scale and at a low cost.

Further, according to a second aspect of the present invention, a microchip includes: a channel extending in an extending direction, wherein an object to be analyzed is capable of traveling through the channel; and deflecting electrodes for deflecting the object in a direction traverse to the extending direction at a vicinity of an analyzing position by being applied with electrical signals thereto.

Therefore, the sample can be transported with certainty along the channel.

Also, the present invention is directed to a manipulating needle for manipulating an object.

According to a third aspect of the present invention, a manipulating needle includes: an edge portion having a diameter not larger than 50 µm, wherein a material having a capability of a biochemical bond with the object or a capability of a biotic bond with the object is adhered to the edge portion.

Therefore, a specific sample can be picked up alone with ease by a simple operation.

Also, the present invention is directed to a manipulator for manipulating an object under a control from an external manipulating apparatus.

According to a fourth aspect of the present invention, a manipulator includes: an edge portion to which a material having a capability of a biochemical bond with the object or a capability of a biotic bond with the object is adhered; and an attachment portion for being detachably attached with the external manipulating apparatus.

Also, the present invention is directed to an analyzing apparatus.

According to a fifth aspect of the present invention, an analyzing apparatus includes: a holder for detachably holding an analyzing microchip, the analyzing microchip including a channel having at least one internal surface, wherein an object to be analyzed is capable of traveling through the channel; and a sensor unit, provided in the holder, for receiving a light from an analyzing position of the channel thereby a light from the object is detected by the sensor when the object travels the analyzing position.

Therefore, the analyzing apparatus can be realized in a small scale and at a low cost.

According to a sixth aspect of the present invention, an analyzing apparatus includes: a holder for detachably holding a microchip, the microchip including: a channel extending in an extending direction, wherein an object to be analyzed is capable of traveling through the channel; and deflecting electrodes at least one of which is provided at a vicinity of an analyzing position; and a controller, provided in the holder, for applying electrical signals to the deflecting electrodes, wherein the deflecting electrodes deflects the object in a direction traverse to the extending direction at the analyzing position when the controller applies the electrical signals to the deflection electrodes.

According to a seventh aspect of the present invention, an analyzing apparatus includes: a holder for detachably holding an analyzing microchip, the analyzing microchip including a channel having at least one internal surface, wherein an object to be analyzed is capable of traveling through the channel; and a lifting unit, provided in the holder, for lifting the analyzing microchip.

Also, the present invention is directed to a method of picking up an object traveling in a traveling direction through a channel formed in an analyzing microchip.

According to an eighth aspect of the present invention, the method includes: sensing the object at an analyzing position of the channel; moving, in response to the sensing of the object, a manipulator into a pick up position of the channel that is downstream side of the analyzing position with respect to the traveling direction, wherein at least a part of the manipulator is made of a material having a characteristic of a biochemical bond capability with the object or a biotic bond capability with the object; and retrieving the object by the manipulator by using the characteristic of the material.

Thus, the present invention has been made in view of the prior art technique, and an object thereof is to provide an analyzing apparatus that can be realized in a small scale and at a low cost, and also to provide a microchip, a sample manipulating needle, and a sample picking up method that can pick up a sample with ease.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 6A and 6B are views each illustrating an example of a voltage waveform that is applied to a piezoelectric element of a linear actuator;

FIG. 7 is a view illustrating an output example of the sensor section;

DESCRIPTION OF THE PREFERRED EMBODIMENTS

Hereafter, preferred embodiments of the present invention will be described with reference to the attached drawings.

1. BASIC CONSTRUCTION OF AN ANALYZING APPARATUS

Figure 1:
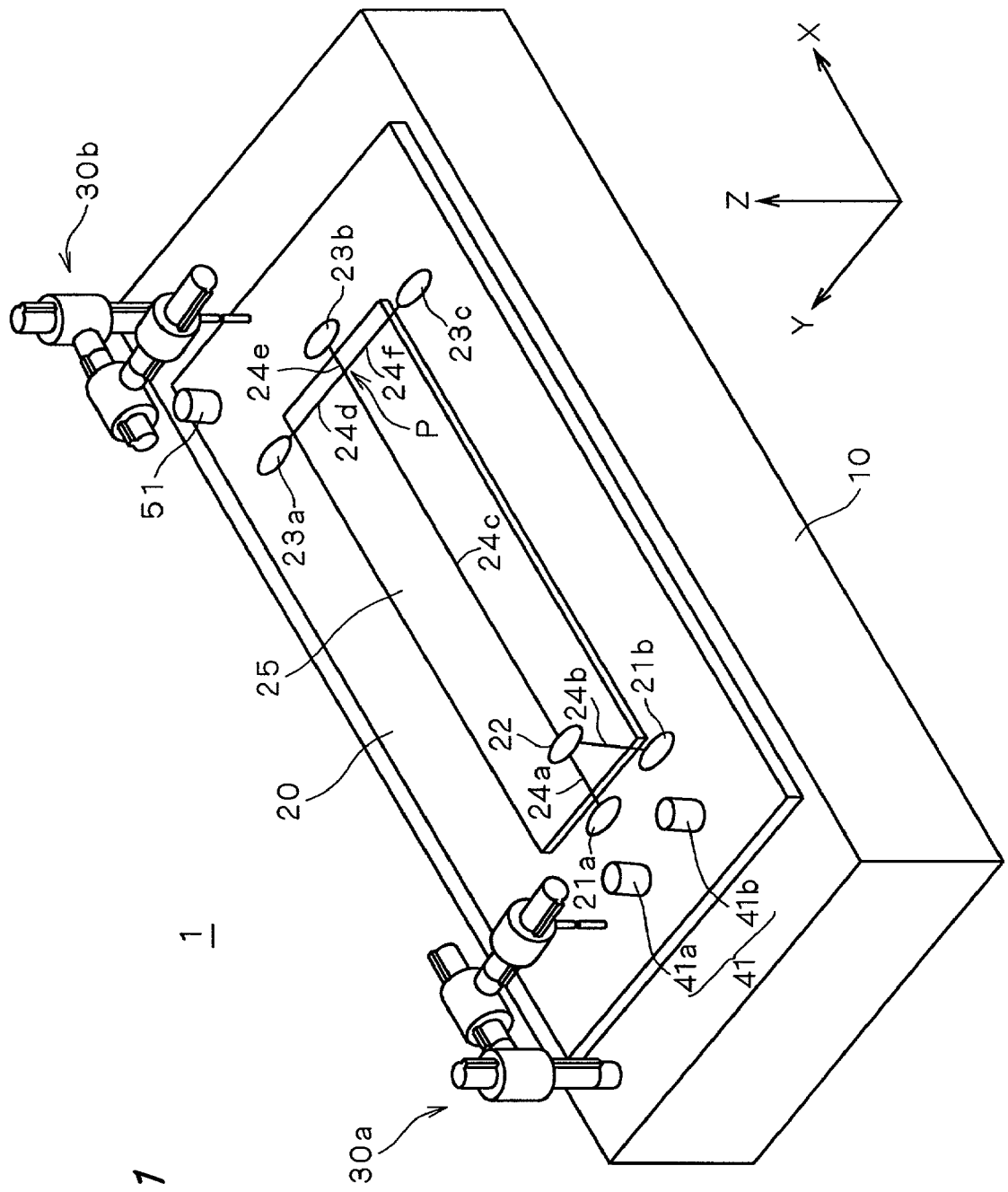
FIG. 1 is a perspective view illustrating a construction example of an analyzing apparatus according to the present invention.

FIG. 1 is a perspective view illustrating a construction example of an analyzing apparatus 1 according to this embodiment. The analyzing apparatus 1 is constructed to include a sensor unit 10, an analyzing chip 20, and micromanipulators 30a, 30b.

A hollowed portion for inserting the flat plate like analyzing chip 20 is formed on the upper surface side of the sensor unit 10 and, at the time of sample analysis, the analyzing chip 20 is inserted into the hollowed portion, whereby the sensor unit 10 and the analyzing chip 20 are integrated together, as shown in FIG. 1.

A plurality of supplying tanks for respectively supplying different samples, a reaction tank for allowing different samples to react in the analyzing chip 20, and a plurality of discharging tanks for discharging the samples having reacted in the reaction tank are formed on the analyzing chip 20. Specifically, referring to FIG. 1, a sample tank 21a for supplying a sample solution containing a sample as an object of analysis, and a reagent tank 21b for supplying a reagent to be used for analysis are formed as the plurality of supplying tanks, and minute channels 24a, 24b are formed from these tanks to the reaction tank 22. Further, an extracting tank 23a for eventually guiding the reaction product as an object of extraction, an exhaust tank 23b for eventually storing unnecessary solutions, and a buffer tank 23c for storing a buffer solution for allowing the reaction product to move towards the extracting tank 23a are formed as the plurality of discharging tanks. The reaction tank 22 and the exhaust tank 23b are connected with each other by minute linear channels 24c, 24e; the extracting tank 23a and the buffer tank 23c are connected with each other by minute linear channels 24d, 24f; and the minute channels 24d, 24f intersect perpendicularly with the minute channel 24c from the reaction tank 22 at an intersection point P.

Each of these tanks is a recess provided on the surface of the analyzing chip 20, and is formed to have the same depth as the minute channels 24a to 24f that are carved in the surface of the analyzing chip. Further, the minute channels 24a to 24f are covered with a cover plate 25, and is formed as a pipe passageway. Here, the minute channels 24a to 24f are each formed to have a width of about 60 μm and a depth of about 10 to 20 μm.

Samples such as a sample solution and a reagent are either directly supplied to each supplying tank on the analyzing chip 20 or put into supplying pots (vessels) 41 that can be easily handled with, such as a sample pot 41a or a reagent pot 41b, and supplied to the sample tank 21a or the reagent tank 21b on the analyzing chip 20 from each pot. Supply of the samples from each pot 41 to each tank is carried out by a first micromanipulator 30a provided for supplying samples. The samples supplied to each supplying tank moves through the minute channel towards the reaction tank and the discharging tank by electrophoresis. The sample as an object of extraction, which has been eventually guided to the extracting tank 23*a*, is stored into the extracting pot 51 by a second micromanipulator 30*b*.

Figure 2:
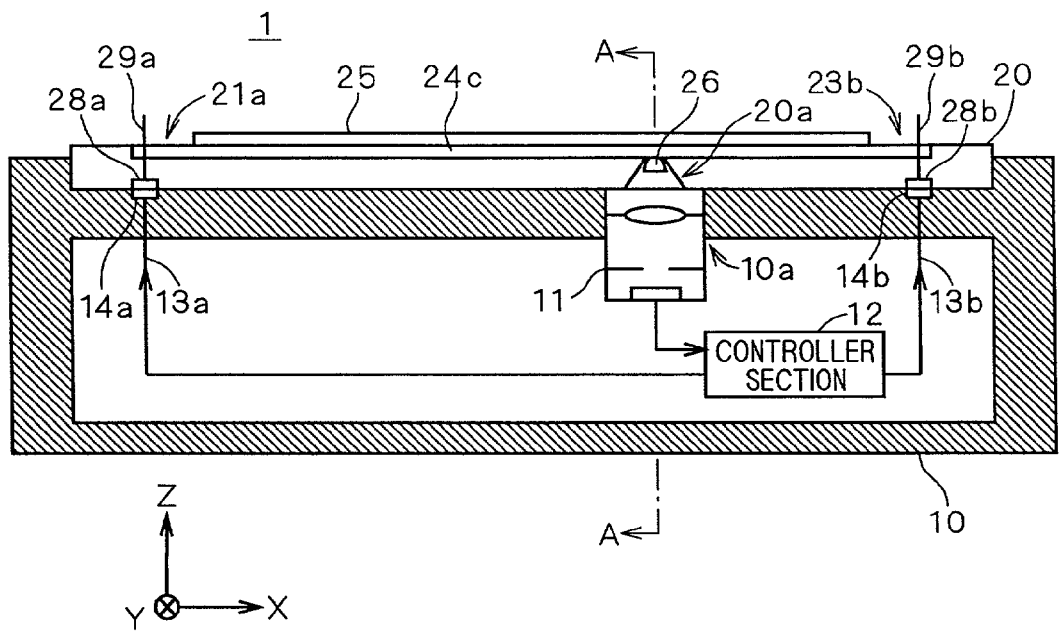
FIG. 2 is a cross section view obtained by cutting a sensor unit with a prescribed plane.

FIG. 2 is a cross section view obtained by cutting the sensor unit 10 with an XZ-plane including the minute channel 24*c*.

Referring to FIG. 2, a hollowed portion for inserting the flat plate-like analyzing chip 20 is formed on the upper surface side of the sensor unit 10 and, on the inner side thereof, a sensor section 11, a controller section 12, and electrodes 13*a*, 13*b* are provided. The sensor section 11 is disposed in an opening 10*a* provided in the hollowed portion, and is constructed to be capable of taking the light on the upper side of the opening 10*a* into the inside. Further, the upper surface sides of the electrodes 13*a*, 13*b* are formed as connectors 14*a*, 14*b* each having a prescribed area. The controller section 12 receives the light detected by the sensor section 11 as electric signals and applies a voltage to each of the electrodes 13*a*, 13*b*.

Here, in FIG. 2, only two electrodes 13*a*, 13*b* are illustrated; however, electrodes controlled by the controller section 12 are provided for each tank formed in the analyzing chip 20.

On the other hand, when the analyzing chip 20 is inserted into the hollowed portion of the sensor unit 10, the connectors 28*a*, 28*b* joined with the connectors 14*a*, 14*b* are formed on the lower surface side of the analyzing chip 20, and electrophoresis electrodes 29*a*, 29*b* that passes through the inside of the analyzing chip 20 to reach near the upper surface of each tank are connected from the connectors 28*a*, 28*b*, respectively. In other words, the electrophoresis electrodes 29*a*, 29*b* are buried in the analyzing chip 20, and one end thereof protrudes into each tank on the analyzing chip 20, and the other end thereof is provided with the connectors 28*a*, 28*b* for giving an electric potential from the sensor unit 10. Further, a tapered hole 20*a* is formed at a prescribed position on the lower side of the minute channel 24*c* formed in the analyzing chip 20, and a condensing optical element 26 is disposed in the hole 20*a*. The position where the condensing optical element 26 is disposed is designed and fabricated so as to be at a position above the sensor section 11 in the sensor unit 10 when the analyzing chip 20 is mounted onto the sensor unit 10.

Therefore, when the analyzing chip 20 is mounted to the sensor unit 10, the connectors 14*a*, 14*b* are joined with the connectors 28*a*, 28*b*, respectively, and the condensing optical element 26 and the sensor section 11 are integrated to perform an optical function, thereby making it possible to perform measurement of fluorescence in the minute channel 24*c* well. Further, in the mounted state such as in FIG. 2, by means of the controller section 12 setting the electrophoresis electrode 29*a* at a low electric potential and setting the electrophoresis electrode 29*b* at a high electric potential, an electric field in the X-direction is generated in the minute channel 24*c*, whereby the sample moves by electrophoresis from the sample tank 21*a* towards the exhaust tank 23*b*.

Details of the principle of the optical function realized by integration of the condensing optical element 26 and the sensor section 11 are described in "Highly efficient detection of surface-generated fluorescence" given in a known document: Applied Optics/Vol. 38, No. 4/1 Feb. 1999 (pp. 724-732). This document describes a method of measuring fluorescence by capturing a fine and weak light with a condensing optical element having a shape obtained by cutting a tip end of a paraboloid of revolution made of glass with a plane being perpendicular to the rotation axis and containing a point near the focal point, and allowing a condensing lens to converge the parallel light, which has been reflected by the paraboloid of the condensing optical element, into an optical detecting element such as an avalanche photodiode.

Figure 3:
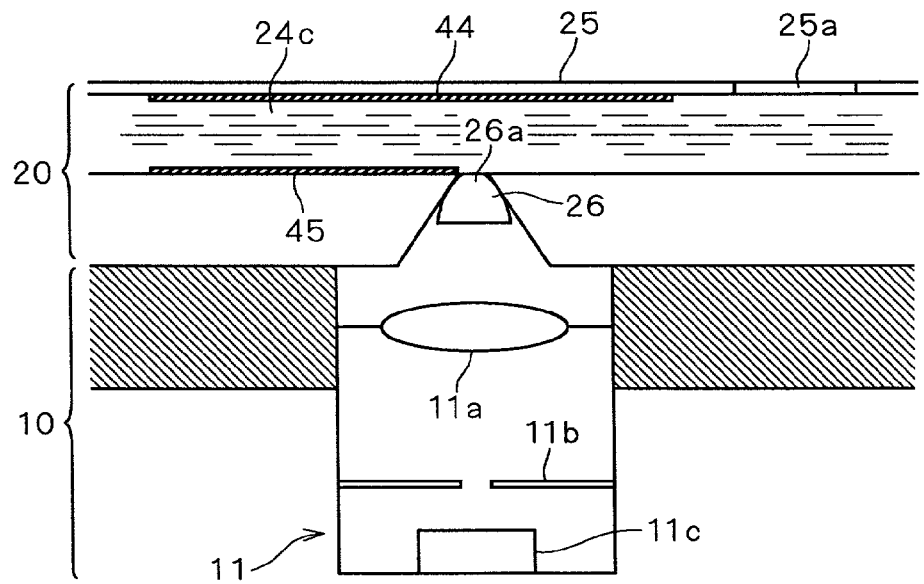
FIG. 3 is an enlarged view around the sensor section of FIG. 2.

In this embodiment also, the fluorescence of the sample is measured by a similar technique. FIG. 3 is an enlarged view around the sensor section 11 of FIG. 2.

Referring to FIG. 3, a condensing optical element 26 for capturing fluorescence from a fluorescent marker adhered to minute particles (samples) such as DNA that migrate through the minute channel 24*c* is mounted at a prescribed position of the minute channel 24*c* of the analyzing chip 20. Further, a condensing lens 11*a*, a mask plate 11*b*, and an optical detecting element 11*c* are provided in the sensor section 11 of the sensor unit 10, and are constructed in such a manner as to be capable of measuring fluorescence from the fluorescent marker adhered to the sample in the minute channel 24*c* by converging the parallel light obtained from the condensing optical element 26 to the optical detecting element 11*c* by means of the condensing lens 11*a*.

The condensing optical element 26 is disposed so that the light-taking surface 26*a*, which is a plane formed by the above-mentioned cutting, faces the minute channel 24*c*, so that the fluorescence can be efficiently captured if the fluorescent marker comes near to the light-taking surface. Particularly, if the fluorescent marker can be approximated within about 100 nm from the light-taking surface 26*a*, the light which is usually reflected by the light-taking surface 26*a* constituting an interface between the solution and the condensing optical element 26 is taken as an evanescent light into the condensing optical element 26 by a so-called near field effect, thereby making it possible to improve an overall sensitivity in the fluorescence measurement. In other words, by approximating a fluorescence-generating sample to a plane containing a point near the focal point, the fluorescence can be captured efficiently into the condensing optical element 26 and, by allowing the light reflected by the paraboloid to be incident into the optical detecting element 11*c* such as an avalanche photodiode by the condensing lens 11*a*, a highly sensitive sensing can be carried out. The light taken into the condensing optical element 26 is reflected by the paraboloid of the condensing optical element 26 and is emitted from the condensing optical element 26 as an approximately parallel light.

A mask plate 11*b* having a pinhole is disposed immediately before the optical detecting element 11*c*, and an image of the pinhole is formed near the light-taking surface 26*a* of the condensing optical element 26 in the analyzing chip 20 so as to cut off a background light from a portion located away from the light-taking surface 26*a*. If a fine and weak light is to be measured, it is essential to separate the background light from the light to be measured. Therefore, by means of the mask plate 11*b*, unnecessary scattered light and excited light can be effectively cut off and, as a result, the SN ratio of the measured value in the sensor section 11 is improved.

The relative position of the condensing optical element 26 on the analyzing chip 20 to the condensing lens 11*a* on the sensor unit 10 side must be precisely set. Therefore, in order that the analyzing chip 20 is mounted to the sensor unit 10 with good precision, it is desirable to control the precision of the outer shape of the analyzing chip 20 and the electrical and optical connecting part thereof to the sensor unit 10 and the precision of the hollowed portion (carved portion) of the sensor unit 10 where the analyzing chip 20 is to be inserted and the electrical and optical connecting part thereof to the analyzing chip 20, strictly within prescribed precision ranges.

Further, in order to raise the condensing efficiency as described above, the fluorescence-generating sample must be approximated within about 100 nm from the light-taking surface 26a of the condensing optical element 26, so that deflecting electrodes 44, 45 are provided near the condensing optical element 26 and in the inside of the minute channel 24c. Namely, the deflecting electrodes 44, 45 perform a function of approximating the sample in the minute channel 24c to the condensing optical element 26.

Further, by applying an electric field between the deflecting electrodes 44, 45, the sample such as DNA can be deflected in a direction traverse to the minute channel 24c. Specifically, the deflecting electrode 44 is disposed at a position facing the minute channel 24c of the cover plate 25, and the deflecting electrode 45 is disposed at an upstream side of the position where the condensing optical element 26 is disposed in the minute channel 24c and on the bottom surface of the minute channel 24c. The electric potential given to these deflecting electrodes 44, 45 are constructed to be controlled from the controller section 12 on the sensor unit 10 side by a joining mechanism with the sensor unit 10 in the same manner as the previously mentioned electrodes for electrophoresis. By setting the deflecting electrode 44 at a lower voltage than the deflecting electrode 45, the controller section 12 can allow the fluorescence-generating sample to migrate to a vicinity of the bottom surface in the minute channel 24c. As a result, the sample can be approximated to the neighborhood of the light-taking surface 26a of the condensing optical element 26. In order to prevent generation of air bubbles by electrolysis of the solution at the deflecting electrode part, particles may be approximated to the condensing optical element by dielectric phoresis due to an electric field gradient generated by applying an alternating current electric field between the deflecting electrodes. Also, the sample can be attracted to the deflecting electrode 45 by the action of the electrophoresis or dielectric phoresis, whereby the intensity and the spectrum of the fluorescence can be measured with precision in a state in which the movement along the minute channel 24c is stopped.

Figure 4:
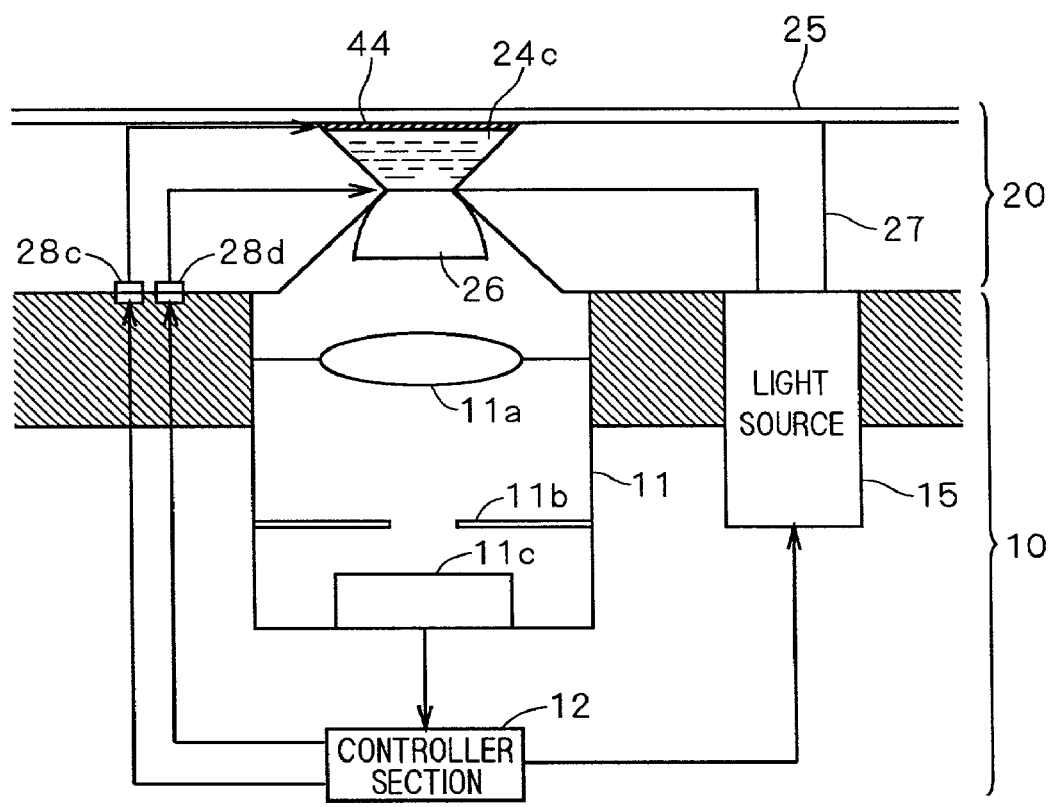
FIG. 4 is an enlarged view around a condensing optical element 26 in the A-A cross section of FIG. 2.

FIG. 4 is an A-A cross section view of the analyzing apparatus 1 in FIG. 2, showing an enlarged view around the condensing optical element 26. Referring to FIG. 4, the minute channel 24c has a trapezoidal cross section in which the upper bottom thereof is longer than the lower bottom thereof, and each side surface is a sloped surface. The electric potential applied to the above-mentioned deflecting electrodes 44, 45 from the controller section 12 is supplied into the minute channel 24c via the connectors 28c, 28d.

Further, referring to FIG. 4, a light source 15 for exciting the fluorescence is provided in the sensor unit 10. The light source 15 for use may be any light source such as a laser, a LED, or a lamp of various type, in accordance with the fluorescent marker to be used. The light source 15 emits a prescribed excited light towards the upper side. In order to guide the excited light from the light source 15 into the minute channel 24c, a light guide 27 is provided as a light guiding means in the inside of the analyzing chip 20. The light guide 27 can be constructed by using an optical fiber buried in the analyzing chip 20 or by providing a wave guide in the analyzing chip 20.

The tip end of the light guide 27 faces the minute channel 24c and, at a position where the light guide 27 is disposed, the light-emitting surface of the light guide 27 is a side wall surface of the minute channel 24c. Further, the light-emitting surface of the light guide 27 is also formed to have a slope similar to that of the side surface of the minute channel 24c. As a result, the light emitted from the light-emitting surface of the light guide 27 generates a refractive action at the light-emitting surface, whereby the excited light is radiated towards the bottom surface side of the minute channel 24c. In other words, it is constructed in such a manner that the excited light is radiated in concentration to the light-taking surface 26a of the condensing optical element 26.

Here, FIG. 4 shows that the light emitted from the light guide 27 is refracted at the side surface of the minute channel 24c to be directed towards the center of the light-taking surface 26a of the condensing optical element 26; however, a microlens or a diffractive optical element may be attached to the end portion of the light guide 27 to control the direction of the excited light and the width of the light beams.

Further, when the fluorescence is measured by the sensor section 11 and it is found out that minute particles (samples) such as DNA, which is an object of extraction, have passed through the channel above the sensor section 11, channels may be switched according to the principle of electrophoresis to guide the sample as an object of extraction to the extracting tank 23a, or the sample may be picked up by means of a micromanipulator 30b to realize a function as an extracting means, whereby the sample as an object of extraction is taken out and utilized for various purposes.

In the case of extraction by switching the channels, the controller section 12 may set the electric potential of the buffer tank 23c shown in FIG. 1 to be lower than the electric potential of the extracting tank 23a and may set the electric potential of the exhaust tank 23b to be a suitable electric potential lower than that of the extracting tank 23a, whereby the sample as an object of extraction is allowed to proceed in the left direction from the intersection point P to be guided to the extracting tank 23a.

Further, by the action of the micromanipulator 30b taking out the solution in the extracting tank 23a and storing the solution into the extracting pot 51, the sample as an object of extraction can be collected in the extracting pot 51.

Thus, by incorporating a super small-scale and highly sensitive fluorescence detecting mechanism into the analyzing apparatus 1, biotic or biochemical analysis such as an analysis of DNA can be performed at a high speed in a small and inexpensive apparatus. In other words, in this embodiment, the mechanism for fluorescence detection is incorporated in the analyzing apparatus 1 which is constructed with the sensor unit 10 and the analyzing chip 20, so that there is no need to dispose an optical system separately around the apparatus. Therefore, the analysis process can be started speedily, and scale reduction and cost reduction can be achieved.

Also, since a highly sensitive fluorescence detecting mechanism is realized, a good analysis can be made even with one molecule or several molecules, thereby reducing the amount of required samples such as a sample as an object of analysis and a reagent to the minimum. For this reason, the analysis from a minute sample can be made and, in the field of analysis of DNA, an amplification work such as polymerase chain reaction (PCR) that is performed in advance can be omitted or the number of repetitions thereof can be reduced.

Also, by providing the micromanipulators 30a, 30b in the analyzing apparatus 1, manipulation of the minute samples (supply or extraction manipulation) can be performed automatically.

Further, in the analyzing apparatus 1, the optical system for detecting fluorescence is set in an optimal state simply by inserting the analyzing chip 20 into the sensor unit 10, so that an adjustment or the like of the optical system does not need time and the preparation time for the sample analysis can be shortened.

2. MICROMANIPULATOR

Here, the construction of the micromanipulators 30a, 30b will be described.

Figure 5:
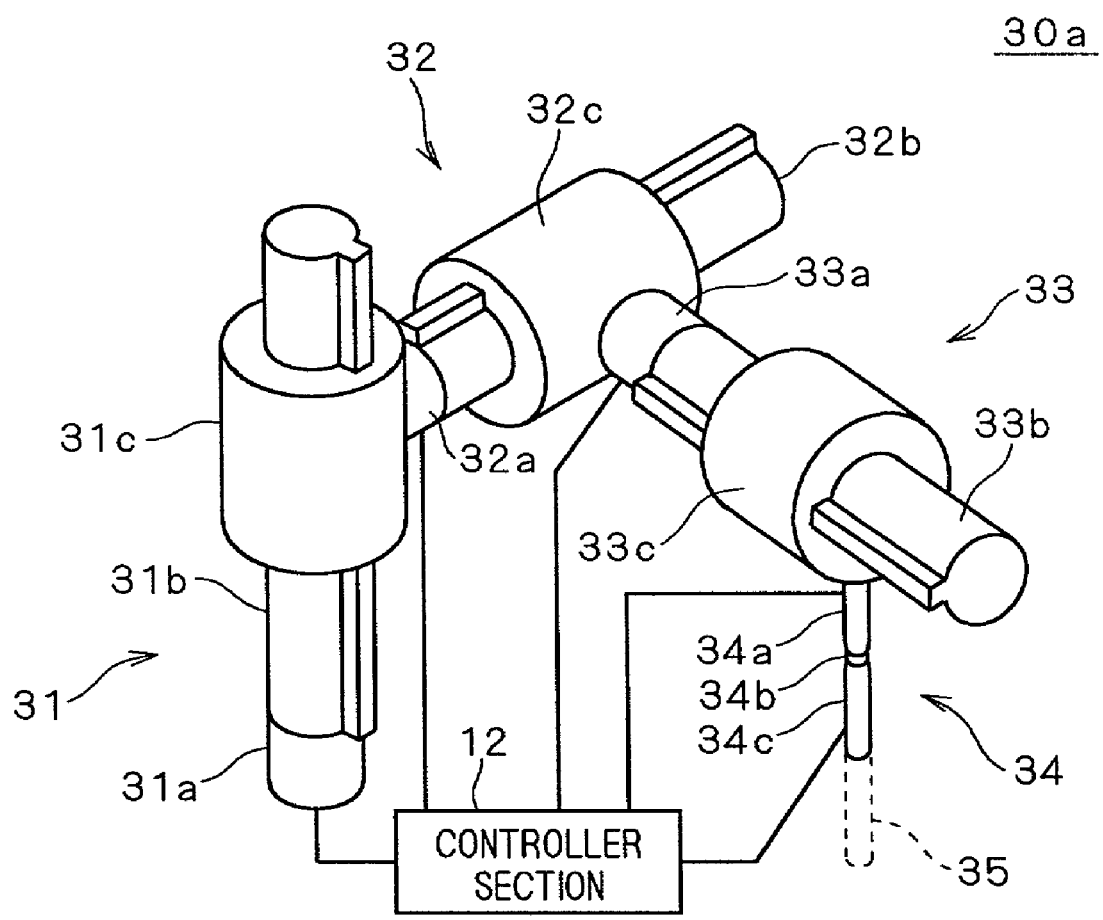
FIG. 5 is a schematic construction view of a micromanipulator.

FIG. 5 is a schematic construction view of the micromanipulator 30a.

The micromanipulator 30a is constructed to include a first linear actuator 31, a second linear actuator 32, a third linear actuator 33, and rotary actuator 34. An end effector 35 is attached to the tip end of the rotary actuator 34 in a freely attachable and detachable manner.

The first to third linear actuators 31 to 33 are sequentially linked so as to perpendicularly intersect with each other, and a plurality of degrees of linear movement freedom is realized. Further, the rotary actuator 34 is constructed to be capable of changing the posture of the end effector 35 coupled to the tip end of the rotary actuator 34 to an arbitrary angle.

The first linear actuator 31 includes a piezoelectric element 31a, a spline shaft 31b, and a slider 31c, and is constructed to be capable of moving the slider 31c along the Z-axis direction.

The piezoelectric element 31a is constructed with laminated piezoelectric ceramics or the like and is connected to the controller section 12. The piezoelectric element 31a performs an elongation and contraction operation along the Z-axis direction by application of a voltage from the controller section 12. One end side of the piezoelectric element 31a is affixed to the fringe side of the sensor unit 10 and the other end side is affixed to the end surface of the spline shaft 31b. Therefore, by the elongation and contraction operation of the piezoelectric element 31a, the spline shaft 31b moves in the Z-axis direction which is the longitudinal direction of the spline shaft 31b.

Further, the slider 31c is fitted into the spline shaft 31b and, since an elastic member mounted in the inside of the slider 31c generates a certain friction between the slider 31c and the spline shaft 31b, the slider 31c is usually in a state of being fixed to the spline shaft 31b. Here, needless to say, the rotation of the slider 31c in the circumferential direction of the spline shaft 31b can be restrained by an engagement of the projection of the spline shaft 31b and the recess of the slider 31c.

The second linear actuator 32 is fixed to the slider 31c of the first linear actuator 31 and, in the same manner as the first linear actuator 31, the second linear actuator 32 is constructed to include a piezoelectric element 32a connected to the controller section 12, a spline shaft 32b, and a slider 32c, and is adapted to be capable of moving the slider 32c along the X-axis direction. Further, the third linear actuator 33 is fixed to the slider 32c of the second linear actuator 32 and, in the same manner as each of the above-mentioned linear actuators, the third linear actuator 33 is constructed to include a piezoelectric element 33a connected to the controller section 12, a spline shaft 33b, and a slider 33c, and to be capable of moving the slider 33c along the Y-axis direction.

Further, the rotary actuator 34 is affixed to the slider 33c of the third linear actuator 33 along the Z-axis direction. The rotary actuator 34 includes a stepping motor 34a, a rotating plate 34b, and a pitch-yaw actuator 34c.

The stepping motor 34a is constructed with a tubular main body having a small diameter, and is fixed to the slider 33c of the third linear actuator 33. The stepping motor 34a is connected to the controller section 12 and is constructed in such a manner that, by energization from the controller section 12 to the stepping motor 34a, the rotating plate 34b linked to a rotor disposed in the inside of the stepping motor 34a rotates around the rotation axis of the stepping motor 34a. Here, in FIG. 5, the rotation axis of the stepping motor 34a is disposed to be parallel to the Z-axis. The stepping motor 34a allows a rotation movement around a rotation axis parallel to the Z-axis among the rotary operations.

One end side of the pitch-yaw actuator 34c is attached to the rotating plate 34b, and the pitch-yaw actuator 34c rotates around the rotation axis of the stepping motor 34a in accordance with the rotation of the rotating plate 34b. Further, a prescribed oblique plate is disposed at the other end of the pitch-yaw actuator 34c and has a construction of a pivot bearing. By energization from the controller section 12 to a wire made of a shape-memorizing alloy stretched in the inside, the wire elongates or contracts, whereby the oblique plate can be tilted in any direction.

Thus, it is constructed in such a manner that, by driving the pitch-yaw actuator 34c, the oblique plate is tilted from a state of being parallel to the XY-plane to any direction and angle. The pitch-yaw actuator 34c makes it possible to perform a rotation operation (pitching) around a rotation axis parallel to the X-axis and a rotation operation (yawing) around a rotation axis parallel to the Y-axis among the rotary operations.

A base side of the end effector 35 of the micromanipulator 30a is connected and disposed at a tip end of the rotary actuator 34. As the end effector 35, those having a mechanism suitable for performing a prescribed manipulation to minute samples such as DNA are adopted. For example, a micropipette capable of storing and ejecting a prescribed amount of solution, a needle having its tip end formed to have a minute diameter of about 1 to 50 μm, and others are used as the end effector 35.

The micromanipulator 30a is constructed as described above; the first to third linear actuators 31 to 33 can move the position of the end effector 35 linearly in the three axis directions of X, Y, Z; and the rotary actuator 34 can rotate the end effector 35 in the three directions of rolling, pitching, and yawing. In other words, the above-mentioned construction realizes a sum of six degrees of freedom, i.e. three degrees of freedom for linearly moving the end effector 35 and three degrees of freedom for rotating the end effector 35. Here, the three degrees of freedom for rotation are realized by a roll angle movement performed by the stepping motor 34a and a pitch angle and yaw angle movement performed by the pitch-yaw actuator 34c.

Therefore, by adopting the construction of the micromanipulator 30a such as described above, the end effector 35 can be moved to any position and also the end effector 35 can be changed to any posture.

Here, the linear movement performed by the first linear actuator 31 will be described. FIGS. 6A and 6B are views illustrating a non-symmetric voltage waveform such as a saw-tooth waveform as an example of the voltage waveform applied to the piezoelectric element 31a. FIG. 6A illustrates a voltage waveform in the case of moving the slider 31c in the +Z direction and FIG. 6B illustrates a voltage waveform in the case of moving the slider 31c in the −Z direction.

In this embodiment, when a negative voltage is applied to the piezoelectric element 31a, the piezoelectric element 31a contracts; conversely, when a positive voltage is applied to the piezoelectric element 31a, the piezoelectric element 31a elongates. The amount of elongation or contraction can be varied by the absolute value of the applied voltage. For this reason, the amount of elongation or contraction can be controlled by controlling the voltage applied to the piezoelectric element 31a. As a result, movement along the Z-axis of the spline shaft 31b can be controlled.

For example, the voltage waveform of FIG. 6A shows a moderate slope in the rising part of the voltage waveform, and shows a sharp slope in the falling part of the voltage waveform. Therefore, at the rising part where the saw-tooth waveform is moderate, the slider 31c is integrated with the spline shaft 31b by a friction force between the spline shaft 31b and the slider 31c, and moves along the Z-axis direction in accordance with the amount of elongation or contraction of the piezoelectric element 31a. On the other hand, at the falling part where the saw-tooth waveform is sharp, the piezoelectric element 31a tends to suddenly return to the original position while a large inertia force is generated in the slider 31c whereby the slider 31c tends to stay at the position after the movement. This inertia force becomes larger than the friction force, whereby sliding occurs between the slider 31c and the spline shaft 31b. As a result, the slider 31c moves in the +Z direction for the sliding length of the slider 31c relative to the spline shaft 31b. Thus, by repeatedly giving a saw-tooth waveform such as shown in FIG. 6A to the piezoelectric element 31a, the slider 31c moves to the +Z direction side stepwise along the spline shaft 31b.

On the other hand, the voltage waveform of FIG. 6B has a polarity opposite to the waveform of FIG. 6A. Therefore, at the rising part where the saw-tooth waveform is moderate, the slider 31c is integrated with the spline shaft 31b by a friction force between the spline shaft 31b and the slider 31c, and moves along the Z-axis direction in accordance with the amount of elongation or contraction of the piezoelectric element 31a. Since the piezoelectric element 31a contracts by being applied with a negative voltage, the piezoelectric element 31a contracts gradually at the moderate rising part of FIG. 6B. On the other hand, at the sharp falling part of FIG. 6B, the piezoelectric element 31a tends to suddenly return to the original state from the contracted state thereby generating a large inertia force in the slider 31c. This inertia force becomes larger than the friction force, whereby sliding occurs between the slider 31c and the spline shaft 31b. As a result, the slider 31c moves in the −Z direction for the sliding length of the slider 31c relative to the spline shaft 31b. Thus, by repeatedly giving a saw-tooth waveform such as shown in FIG. 6B to the piezoelectric element 31a, the slider 31c moves to the −Z direction side stepwise along the spline shaft 31b.

Thus the first linear actuator 31 is constructed in such a manner that, by reciprocating the piezoelectric element 31a serving as a driving means at non-symmetric speeds, the first linear actuator 31 can reciprocate the spline shaft 31b connected to the piezoelectric element 31a, whereby the slider 31c is capable of relative inertia movement. Here, if the applied voltage in driving the piezoelectric element 31a is strictly controlled, the amount of movement for which the slider 31c moves by one slide can be controlled to an almost constant value. In other words, if the voltage level or the slope of the waveform of the applied voltage is controlled, the amount of movement for which the slider 31c moves by one slide can be varied. For example, if the voltage level is set high and the slope of the sharp falling part is made sharper, the amount of movement caused by one slide increases, whereby the end effector 35 can be moved at a high speed. Conversely, if the voltage level is set low and the slope of the sharp falling part is made a little moderate, the amount of movement caused by one slide decreases, whereby the end effector 35 can be moved little by little at a low speed.

Further, if a saw-tooth waveform such as mentioned above is continuously applied to the piezoelectric element 31a, the operation of the slider 31c will be a rough movement of stepwise motion. On the other hand, by controlling the voltage value applied to the piezoelectric element 31a, the piezoelectric element 31a shows an amount of elongation or contraction corresponding to the voltage value, so that the operation of the slider 31c will be a fine movement of continuous motion in a minute range. Therefore, by using a piezoelectric element as a source of driving the linear actuator, the rough movement and the fine movement can be used separately, whereby the position precision of the slider 31c can be enhanced.

Here, by forming a magnetization pattern forming portion at the projecting part of the spline shaft 31b and further disposing a magnetic resistance element or the like in the inside of the slider 31c, they are integrated to construct a linear encoder, and a pulse signal can be generated from the magnetic resistance element in accordance with the amount of movement of the slider 31c. By performing a prescribed operation based on the pulse signal, the position of the slider 31c relative to the spline shaft 31b can be detected, and the movement can be controlled on the basis of this position.

As shown above, the operation of the first linear actuator 31 has been described; however, the second linear actuator 32 and the third linear actuator 33 have the same construction and operation as the first linear actuator 31. Further, in the above, description has been made taking the micromanipulator 30a as an example; however, the micromanipulator 30b is also constructed in the same manner and its operation is the same.

These micromanipulators 30a, 30b are disposed at two end sides of the side of supplying the samples and the side of extracting the samples in the sensor unit 10, as shown in FIG. 1, and are constructed in such a manner that an electric controlling signal is supplied to each actuator by the controller section 12 in the sensor unit 10.

Furthermore, the micromanipulators 30a, 30b such as described above can be housed in a size of about 20 mm cube and can control the end effector 35 with a resolution of around 1 μm, so that the micromanipulators 30a, 30b can be incorporated in the apparatus to perform operations of precision without enlarging the size of the analyzing apparatus 1.

3. ANALYZING OPERATION IN THE ANALYZING APPARATUS

Returning to FIG. 1, samples such as a sample solution and a reagent supplied by the sample pot 41a and the reagent pot 41b are supplied respectively to the sample tank 21a and the reagent tank 21b in required amounts by the first micromanipulator 30a mounted to an end of the sensor unit 10. A micropipette capable of putting a prescribed amount of solution in and out is attached to the tip end of the micromanipulator 30a, whereby solutions can be supplied from each pot to each tank.

The minute channels 24a to 24f of the analyzing chip 20 are filled with a solution such as a buffer liquid in advance to expel air from the channels so that the supplied sample or reagent can immediately move in the minute channels 24a to 24f by a method such as electrophoresis.

The sample and the reagent supplied to the sample tank 21a and the reagent tank 21b move downstream (towards the direction of the exhaust tank 23b) through the minute channels 24a to 24f by electrophoresis. At this time, the sample tank 21a and the reagent tank 21b are set at a lower electric potential than the exhaust tank 23b to generate an electric field that is oriented to an upstream of the minute channels 24a to 24c so that a flow is generated by electrophoresis in a direction opposite to the electric field. The sample and the regent meet and react in the reaction tank 22.

Here, a description will be given on a case in which a solution of plural kinds of DNA fragments cut by a restriction enzyme is used as the sample solution and a solution of plural kinds of probe DNA labeled with a fluorescent marker and having a base sequence that is complementary to the plural kinds of DNA fragments in the sample solution is used as the reagent.

When prescribed solutions are supplied to the sample tank 21a and the reagent tank 21b, the sample and the reagent move towards the reaction tank 22 by electrophoresis caused by an electric field applied between the sample tank 21a and the reagent tank 21b and the reaction tank 22. In the reaction tank 22, a portion of the sample DNA constructed with the DNA fragments and the probe DNA having complementary base sequences hybridize with each other. The DNA that has hybridized and the DNA that has not hybridized in the reaction tank 22 move downstream (in the direction of the exhaust tank 23b) through the minute channel 24c by electrophoresis caused by the electric field applied between the reaction tank 22 and the exhaust tank 23b. The minute channel 24c between the reaction tank 22 and the intersection point P is filled with a polymer such as polyacrylamide and is constructed to be capable of giving a difference in the phoresis speed in accordance with the size of the DNA that migrates by electrophoresis.

If the lengths of the probe DNAs in the reagent are about the same, the probe DNAs that have not hybridized move at about the same speed through the minute channel 24c by electrophoresis. The DNA fragments (sample DNA) that have not hybridized move through the minute channel 24c at a speed corresponding to their length.

On the other hand, those obtained by hybridization of the probe DNA and the sample DNA have a double chain in the hybridized portion and have a one-chain nucleotide before and after the hybridized portion, constituting a long DNA fragment as a whole. Therefore, those obtained by hybridization move through the minute channel 24c at a slower speed than the probe DNA or the sample DNA that has not hybridized. The type of the DNA fragments in the sample DNA can be analyzed by measuring the difference in the speed of electrophoresis by setting a position of cutting with a restriction enzyme and a base sequence of the probe DNA to be hybridized so that the length of the hybridized DNA will vary depending on the type of the DNA fragments in the sample.

Since a sensing position (position at which the condensing optical element 26 is to be disposed) for measuring the fluorescence of the fluorescent marker attached to the probe DNA is set at a prescribed position on a little upstream side from the intersection point P of the minute channel 24c, the time at which the probe DNA that has not hybridized passes through the sensor section 11 and the time at which the plural kinds of products obtained by hybridization of the probe DNA and the sample DNA pass through the sensor section 11 can be determined from the output of the optical detecting element 11c in the sensor section 11. Since the DNA fragments (sample DNA) that have not hybridized do not have a fluorescent marker, they do not affect the sensor output.

FIG. 7 is a view showing an output example of the sensor section 1. In this example, the probe DNA that has not hybridized passes through the sensing position at a comparatively early time t1 after the start of the measurement, and at that time, the first output peak PK1 appears. Thereafter, a plurality of peaks PK2, PK3, PK4 appear at the time t2, t3, t4, respectively. In other words, plural kinds of products obtained by hybridization of the probe DNA and the sample DNA pass through the sensing position with a time difference corresponding to the difference in length with time intervals after the probe DNA that has not hybridized passed through the sensing position, whereby the plural peaks PK2 to PK4 appear. The time of appearance of the peak is determined in accordance with the length of each product, and the size of the peak is determined in accordance with the amount of each product. Therefore, the type and other characteristics of the product can be found out by analyzing the output example of FIG. 7. Thus, if there are three types of hybridized products, peaks PK2, PK3, PK4 appear due to the hybridized products as shown in FIG. 7.

Further, by any combination of the selection of a restriction enzyme and the design of the base sequence of the probe DNA, base sequence information such as the presence of gene modification or one-base polymorphism of the DNA as an object of analysis can be obtained.

Further, if the fluorescent marker for labeling the probe DNA is changed for each type of the probe and the sensor section 11 is constructed to have a spectrum function, the type of the hybridized product can be distinguished by classifying the wavelength of the fluorescence of the marker. In this case, the time at which the hybridized product passes through the sensing position need not be precisely measured, and it is sufficient to distinguish between the peak of the probe DNA that has not hybridized and the peak of the hybridized product in time.

Thus, if it is found that the product as an object of extraction has passed through the sensing position as a result of measurement of the fluorescence in the sensor section 11, control is made to take out an object product by switching the minute channels using the above-mentioned principle of electrophoresis to guide the product as an object of extraction to the extracting tank 23a or by picking up the product with the micromanipulator 30b.

4. TAKING OUT THE SAMPLE

Here, a method of taking out a sample such as DNA from a minute channel by picking up will be described.

Figure 8:
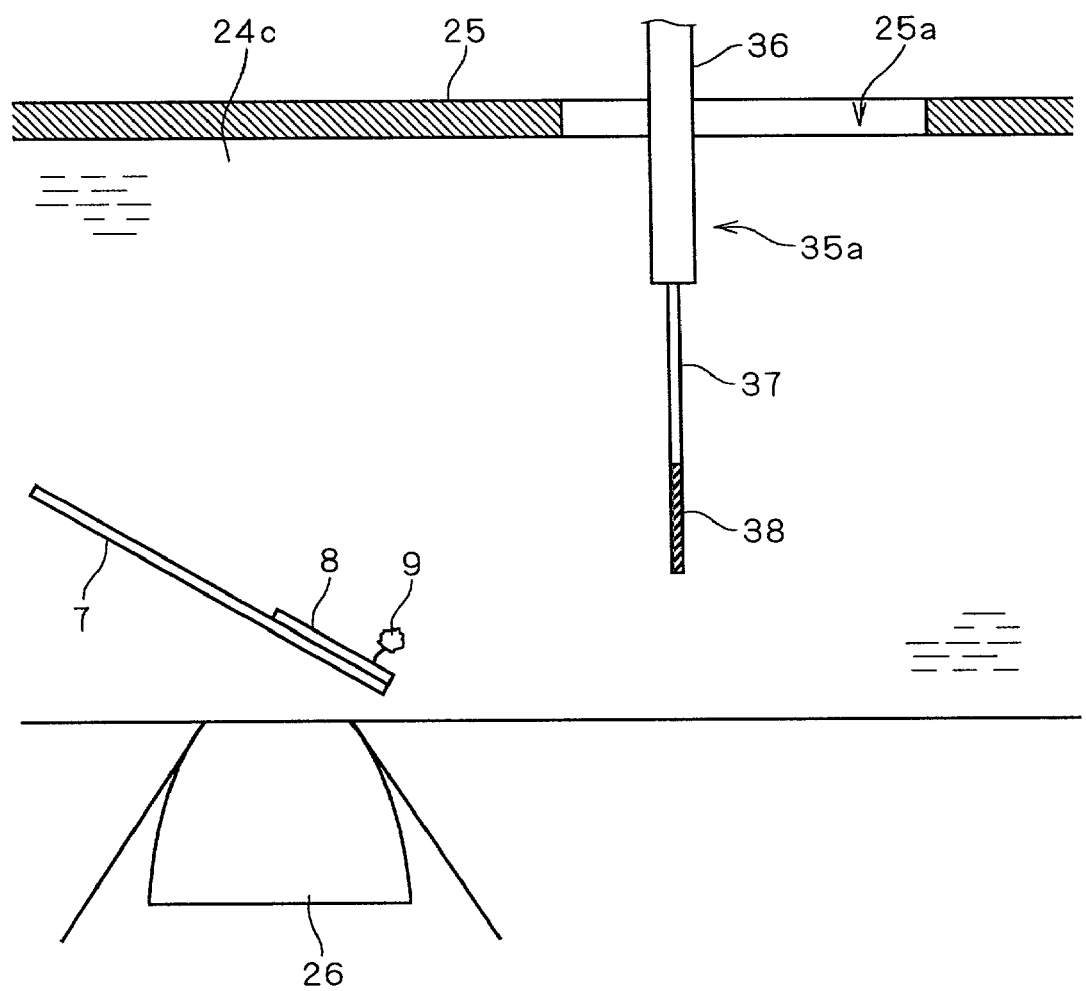
FIG. 8 is a view illustrating a method of picking up a sample in a minute channel.

FIG. 8 is a view illustrating a method of picking up DNA in a minute channel. A sample operating needle 35a is used as the end effector that is joined with the tip end of the micromanipulator 30b. The sample operating needle has a base portion 36 and a needle 37 having a small diameter and protruding from the base portion 36. The needle 37 may be made by fine processing of metal or made of whiskers. In order to reduce the turbulence of the flow of solution in the minute channel 24c, at least a tip end portion of the needle 37 that is dipped into the solution is preferably narrowed to about 1 μm to 50 μm. A capturing DNA 38 is adhered to the tip end of the needle 37. The adhesion of the capturing DNA 38 to the tip end of the needle 37 can be performed by a chemical technique. An example of this technique is disclosed in U.S. Pat. No. 5,789,167 as a process for bonding a probe DNA. For example, in this example, a method can be utilized in which an end portion of a polypeptide spacer is bonded to the capturing DNA and the needle 37 by covalent bond.

In FIG. 8, the sensor section 11 detects the movement of the DNA (object DNA) 7 as an object of extraction in the minute channel 24c in a state of being hybridized with the probe DNA 8 having a fluorescent marker 9 attached thereto. At this time, on the basis of the detection result by the sensor section 11, the controller section 12 controls the micromanipulator 30b, and allows the sample operating needle 35a, which is attached as an end effector of the micromanipulator 30b, to be dipped into the solution in the minute channel from a small hole 25a provided in the cover plate 25 on the minute channel 24c. As described above, the tip end (needle 37) of the sample operating needle 35a is formed to have a minute diameter, and a substance having a biotic or biochemical bond capability with the sample to be extracted is adhered to its tip end. The sample to be extracted can be taken out from the solution by dipping the needle 37 in the solution, reacting and bonding the substance adhered to the needle 37 with the sample to be extracted in the solution, and thereafter controlling the operation of the micromanipulator 30b with a control signal from the controller section 12 to take out the needle 37 from the solution.

In this embodiment, the capturing DNA 38 that hybridizes with an object DNA to be extracted is adhered to the needle 37 of the sample operating needle 35a, and the product to be extracted is captured by reacting (hybridizing) the object DNA contained in the product in the minute channel 24c with the capturing DNA 38.

In other words, by dipping the needle 37 of the sample operating needle 35a into the solution, the capturing DNA 38 adhering to the tip end of the needle 37 hybridizes with the product in the solution, whereby only the object sample can be extracted from the solution. At this time, if the operation of the micromanipulator 30b is controlled by the controller section 12 so that the tip end of the sample operating needle 35a scans the cross section of the minute channel 24c, the probability of the capturing DNA 38 hybridizing with the object DNA can be increased to ensure a more certain take-out of the object sample.

As described above, the DNA picked up from the minute channel 24c is conveyed into the extracting pot 51 by the operation of the micromanipulator 30b, and is stored in the extracting pot 51.

Several processes can be considered when the sample is transported to the extracting pot 51.

As an example, there is a process such that a buffer solution is put into the pot in advance, and a hybridized DNA is dipped into the buffer solution together with the sample operating needle 35a. By raising the temperature of the liquid contained in the pot, the bond between the probe DNA and the object DNA is released to make a state in which the object DNA hybridized with the capturing DNA is adhering to the sample operating needle 35a. Then, the sample operating needle 35a is moved to a different pot filled with a buffer solution and, by raising the temperature of the liquid contained in the pot, the bond between the object DNA and the capturing DNA is released to allow only the object DNA to be present in the solution. In this case, it is necessary to design the base sequences of the probe DNA and the capturing DNA in accordance with the base sequence of the object DNA so that the bond between the probe DNA and the object DNA is released at a lower temperature than the bond between the capturing DNA and the object DNA. Then, the temperature raised in the second pot is set higher than the temperature raised in the first pot thereby to release the two bonding sites of the object DNA in a desired order.

As another example, the picked-up DNA is heated together with the sample operating needle 35a in the buffer solution of the extracting pot 51 to release the bond between the capturing DNA and the object DNA, thereby to allow the object DNA bonded to the probe DNA to be present in the buffer solution. If the base sequence of the probe DNA is designed to be capable of being used also as a primer for amplification of the object DNA by polymerase chain reaction (PCR), the object DNA can be amplified simply by adding a polymerase enzyme and oligonucleotide into the extracting pot 51 and controlling the temperature.

Figure 9:
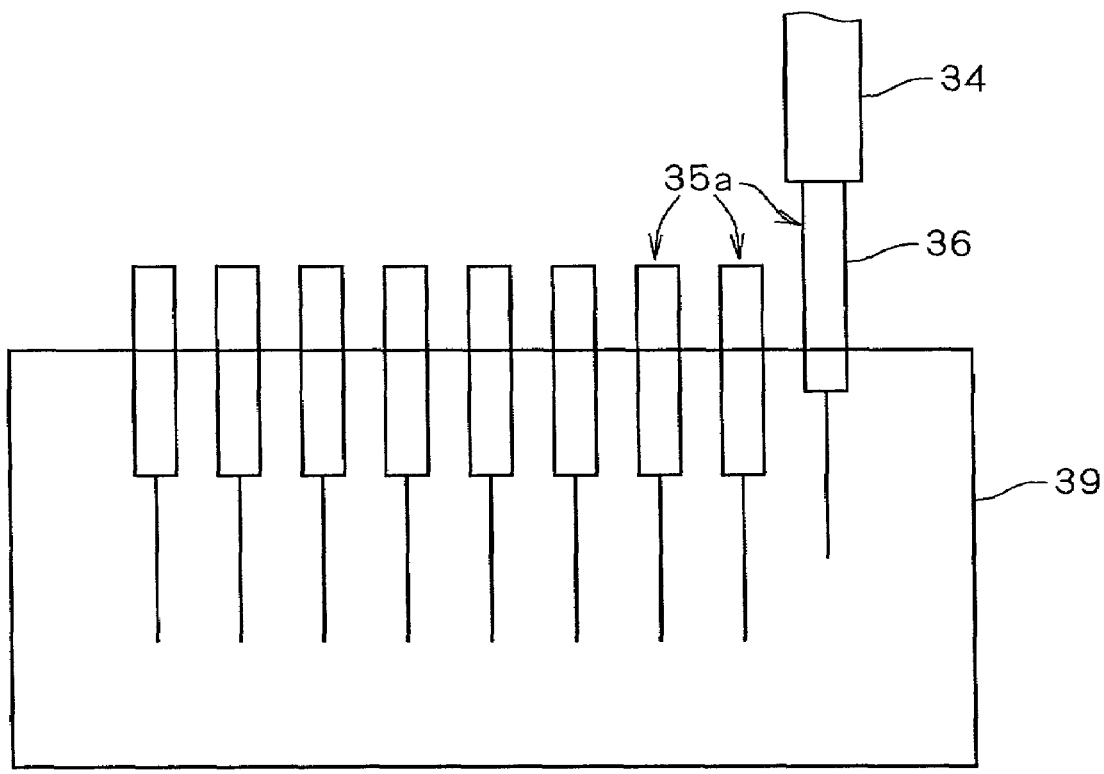
FIG. 9 is an explanatory view of a mechanism for exchanging sample manipulating needles of a micromanipulator.

FIG. 9 is a view for describing a mechanism of exchanging the sample operating needles 35a of the micromanipulator 30b.

Referring to FIG. 9, a plurality of sample operating needles 35a are stored by being inserted into a holder 39. A preserving liquid is put in a prescribed amount into the holder 39 in accordance with the needs to dip the needle point of the sample operating needles 35a. At the time of use, the controller section 12 controls the operation of the micromanipulator 30b to bond the base portion 36 of the sample operating needle 35a with the tip end of the rotary actuator 34 of the micromanipulator 30b. If the base portion 36 of the sample operating needle 35a is formed of a magnetic material and a magnet or a electromagnet is disposed at the tip end of the rotary actuator 34 of the micromanipulator 30b, the sample operating needle 35a can be easily bonded with the tip end of the rotary actuator 34 of the micromanipulator 30b. Further, by providing a recess for inserting the base portion 36 of the sample operating needle 35a into the tip end of the rotary actuator 34 in the micromanipulator 30b, the sample operating needle 35a can be mounted so as not to waver during the operation. A precise position control can be made by the micromanipulator 30b if the shapes of the base portion 36 and the needle 37 are controlled with a prescribed precision in the sample operating needle 35a.

Further, when the controller section 12 allows the micromanipulator 30b to access an arbitrary sample operating needle among the plurality of sample operating needles 35a inserted into the holder 39 and moves the tip end of the rotary actuator 34 to an upper side of the base portion 36, the sample operating needle can be mounted to the micromanipulator 30b.

On the other hand, in exchanging the sample operating needles, the operation control performed by the controller section 12 allows the micromanipulator 30b to insert a used sample operating needle 35a into a site of the holder 39 where the sample operating needles 35a are not inserted, and to perform a prescribed operation to remove the used sample operating needle 35a. Thereafter, an operation similar to that performed in the above-mentioned mounting is carried out, whereby the sample operating needles 35a can be exchanged.

Here, the holder 39 may be mounted at any position which the micromanipulator 30b of the sensor unit 10 can access.

The above description has been given on the case in which the end effector 35 is a sample operating needle 35a; however, it is needless to say that the end effectors 35 are not limited to sample operating needles 35a, and the end effectors 35 can be automatically mounted and automatically exchanged, for example, by using a holder 39 for other end effectors such as micropipettes. Further, by disposing the holder 39 for storing a plurality of end effectors 35 at a position which each of the micromanipulators 30a, 30b can access, a continuous process can be carried out while automatically exchanging the end effectors 35 even if different analyzing processes are to be repeatedly carried out in the analyzing apparatus 1.

Here, the above sample operating needle 35a is not limited to the case in which the micromanipulator 30b picks up a specific sample, but has a structure suitable also for a case in which a person performs a manual operation to pick up a specific sample from within the minute channel.

5. MECHANISM FOR PERFORMING AN AUTOMATIC OPERATION OF THE ANALYZING APPARATUS

As described previously with reference to FIG. 1, the analyzing apparatus 1 is constructed in such a manner that the sample is supplied by using a supplying pot 41 and the sample is taken out and stored by using an extracting pot 51. In such a case where the sample is supplied or extracted by using pots and where the analyzing and extracting operations are carried out continuously and automatically while exchanging plural kinds of samples and reagents, a pot exchanging mechanism is preferably added as an optional device to the analyzing apparatus 1 shown in FIG. 1. In this case, by mounting a plurality of sample pots, reagent pots, and others in the pot exchanging mechanism, analysis work can be automatically performed for plural times while exchanging the samples or reagents. The same applies to the extracting pots, and by mounting a plurality of extracting pots, analysis and extraction work can be automatically carried out by storing a different extract into each extracting pot while exchanging the extracting pots every time a sample to be extracted is guided to the extracting tank 23a.

Figure 10:
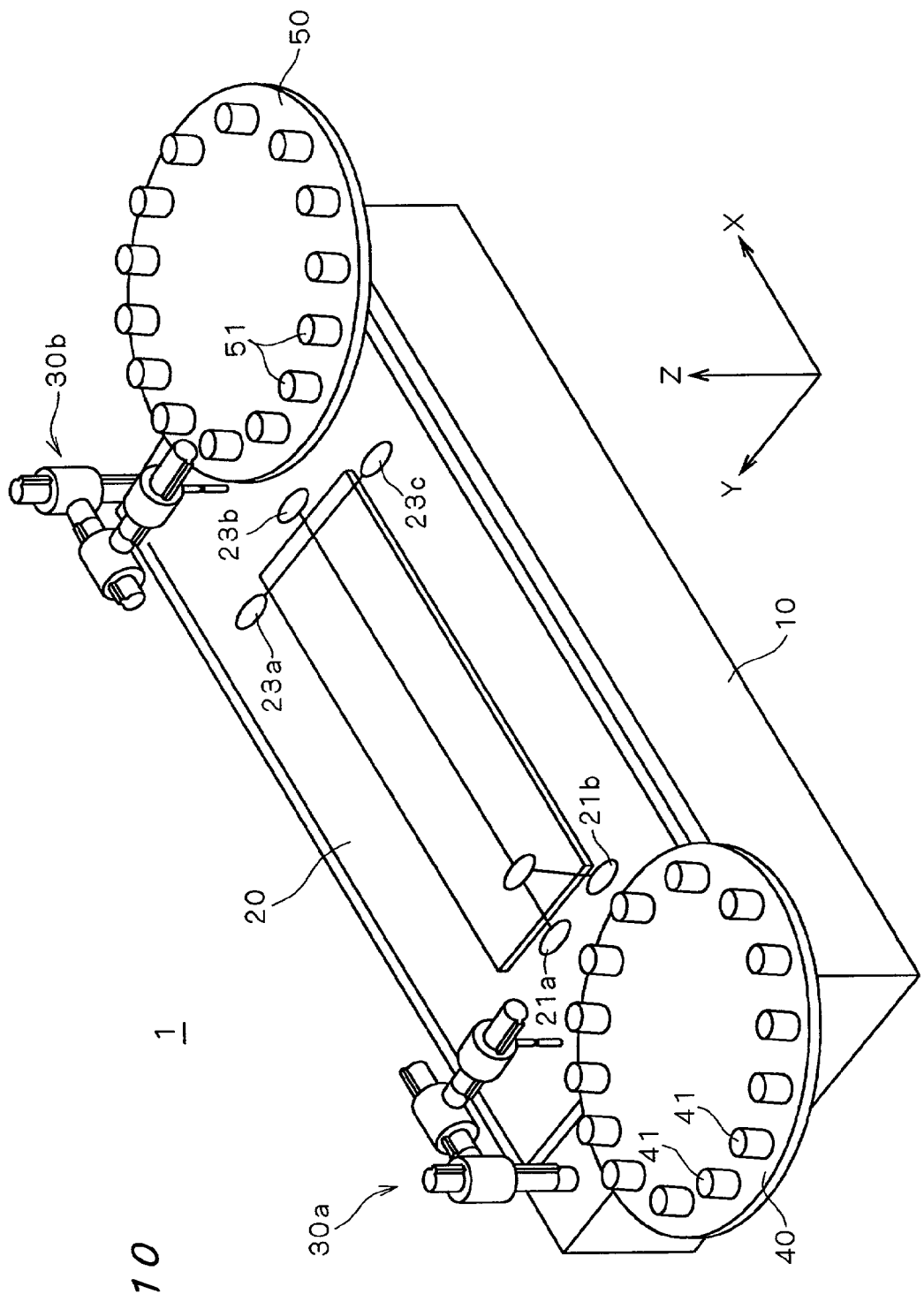
FIG. 10 is a perspective view illustrating an analyzing apparatus to which a pot exchanging mechanism is added.

FIG. 10 is a perspective view illustrating an analyzing apparatus 1 to which a pot exchanging mechanism has been added. Referring to FIG. 10, the analyzing apparatus 1 includes a rotatable supplying disk 40 having a plurality of supplying pots 41 mounted thereon, and a rotatable extracting disk 50 having a plurality of extracting pots 51 mounted thereon in addition to the construction shown in FIG. 1.

A plurality of sample pots and reagent pots are mounted on the rotatable supplying disk 40, and a rotating motor (not illustrated) is provided as a rotation driving source of the supplying disk on the lower side (rear side) of the central position of the disk. This rotating motor is connected to the controller section 12 in the inside of the sensor unit 10. By controlling the rotating motor with the controller section 12 to control the rotation phase angle of the supplying disk 40, desired sample pot and reagent pot can be moved near to the sample tank 21a and the reagent tank 21b on the analyzing chip 20. When the movement of the desired pots is completed, the micromanipulator 30a is operated to supply the sample and the reagent to each tank on the analyzing chip 20. Further, in order to perform a different reaction on the chip, a plurality of reactions can be carried out automatically by rotating the supplying disk 40 and supplying a sample pot and a reagent pot to the analyzing chip 20 while suitably exchanging the sample pots and the reagent pots.

Similarly, a plurality of extracting pots 51 are mounted on the rotatable extracting disk 50, and a rotating motor (not illustrated) is provided as a rotation driving source of the extracting disk on the lower side (rear side) of the central position of the disk. This rotating motor also is connected to the controller section 12 in the inside of the sensor unit 10. By controlling the rotating motor with the controller section 12 to control the rotation phase angle of the extracting disk 50, a desired extracting pot can be moved near to the extracting tank 23a on the analyzing chip 20. When the movement of the desired pot is completed, the micromanipulator 30b is operated to move the samples such as particles and reaction products as an object of extraction from the extracting tank 23a to the extracting pot 51. Furthermore, if a different reaction has been carried out on the chip, the extracting disk 50 is rotated to exchange the extracting pots 51 and the sample as an object of extraction is moved to the extracting pot 51.

Thus, by providing a supplying disk 40 and an extracting disk 50 capable of mounting a plurality of pots as a pot exchanging mechanism, an analysis and extraction work can be carried out continuously and automatically for plural times.

On the other hand, there is a case in which the number of use of the analyzing chip 20 comes to a limit or the analyzing chip 20 must be replaced due to change in the contents of analysis. Therefore, an analyzing chip exchanging mechanism is preferably added as an optional device to the analyzing apparatus 1 of FIG. 1. In this case, by mounting a plurality of analyzing chips 20 beforehand in the analyzing chip exchanging mechanism and by automatically exchanging the analyzing chips 20 to be mounted on the sensor unit 10 in accordance with the needs, an analysis work can be carried out continuously and automatically for plural times. Further, a continuous and automatic operation using the analyzing chip exchanging mechanism and the above-mentioned pot exchanging mechanism in combination is also possible.

Figure 11:
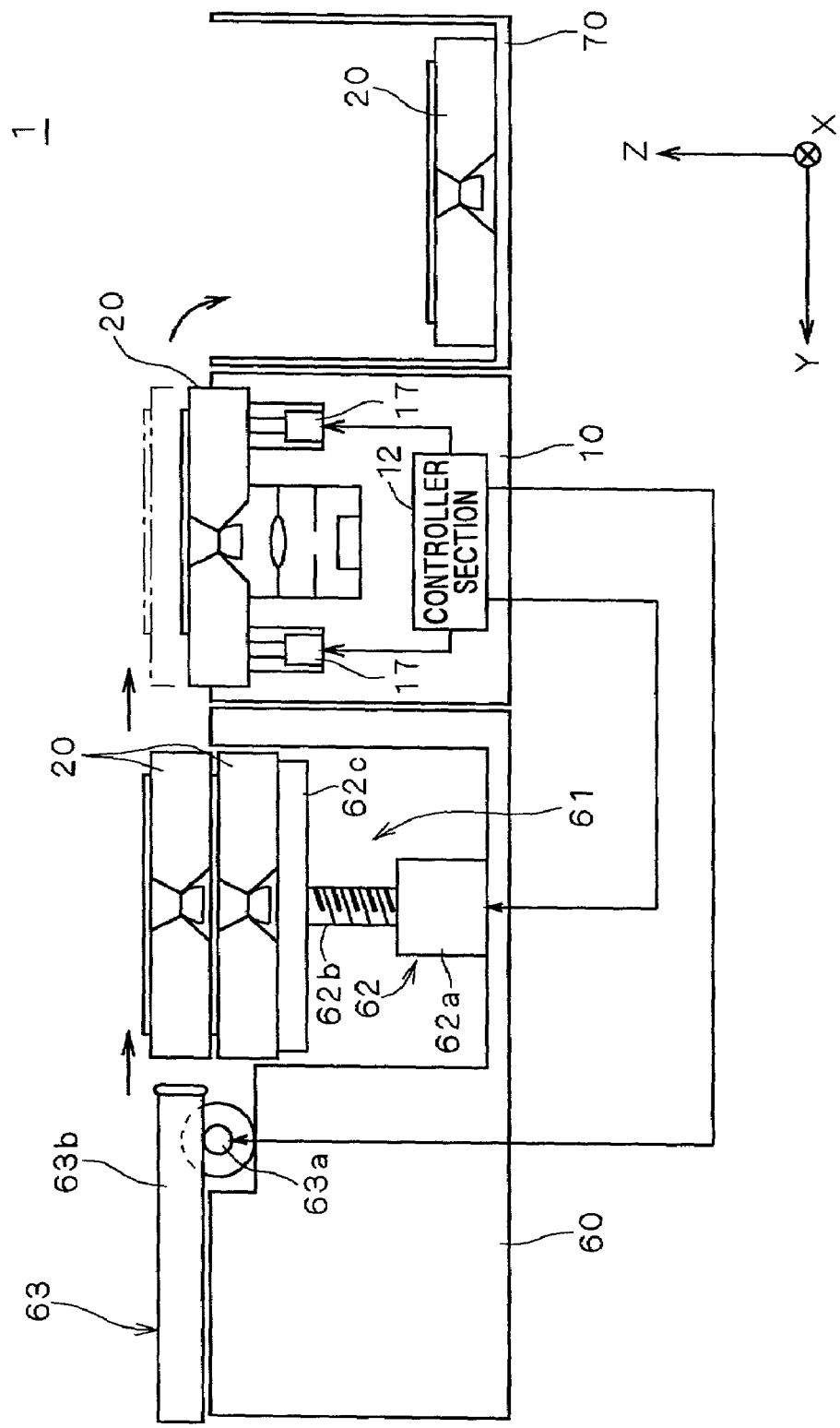
FIG. 11 is a view illustrating a construction example of analyzing apparatus in which an analyzing chip exchanging mechanism is disposed.

FIG. 11 is a view illustrating a construction example of an analyzing apparatus 1 in which an analyzing chip exchanging mechanism is disposed. Here, FIG. 11 is a view in which the analyzing apparatus 1 is viewed from a certain point in the direction perpendicular to the YZ-plane of FIG. 1, and illustration of the micromanipulators 30a, 30b is omitted.

In the analyzing apparatus 1 shown in FIG. 1, a stacker 60 and a collector 70 are disposed along the Y-axis direction with the sensor unit 10 sandwiched therebetween.

A pushing-up actuator 17 driven and controlled by the controller section 12 is disposed at a prescribed lower position of the analyzing chip 20 mounted onto the sensor unit 10. In exchanging the analyzing chips 20 on the sensor unit 10, the controller section 12 in the sensor unit 10 operates the pushing-up actuator 17, and lifts the analyzing chip 20 from the hollowed portion in the upper part of the sensor unit 10 (the carved part for inserting the analyzing chip 20). At this time, the position of the lower surface of the analyzing chip 20 is set to be higher than the height of the bank of the hollowed portion of the sensor unit 10. As the push-up actuator 17, a plunger-type magnet, for example, can be utilized.

A storing section 61 for storing unused analyzing chips 20, a chip elevator 62 disposed at a lower part of the storing section 61, and a chip pushing-out mechanism 63 for pushing the analyzing chip 20 out to the hollowed portion of the sensor unit 10 are provided in the stacker 60. In exchanging the analyzing chips 20, the chip elevator 62 is operated to lift the analyzing chips 20 up so that the position of the lower surface of the uppermost analyzing chip 20 among the plurality of analyzing chips 20 stored in the storing section 61 will be a little higher than the bank of the hollowed portion of the sensor unit 10. Thereafter, the chip pushing-out mechanism 63 is operated to push the analyzing chip 20 out to a position above the hollowed portion of the sensor unit 10. When the amount of pushing-out the analyzing chip 20 by the chip pushing-out mechanism 63 exceeds a prescribed amount, the push-up actuator 17 of the sensor unit 10 stops, and the pushing-up member returns to the state before the start of the operation. When the analyzing chip 20 reaches the hollowed portion of the sensor unit 10, the analyzing chip 20 falls into the hollowed portion by its self-weight, whereby the analyzing chips 20 are exchanged. The analyzing chip 20 mounted to the sensor unit 10 is pushed out by the tip end of the unused analyzing chip 20, which has been pushed out from the stacker 60, to move from above the sensor unit 10 towards a place where the collector 70 is disposed, and is let fall into the collector 70 by its self-weight.

By adopting the above-mentioned construction, the analyzing chips 20 mounted on the sensor unit 10 can be automatically exchanged in accordance with the needs, whereby the analysis work can be carried out continuously and automatically for plural times.

Here, as the above-mentioned chip elevator 62, a mechanism of lifting the elevator floor 62c up and down by combining a micromotor 62a and a thread mechanism 62b can be utilized, for example. Further, the chip pushing-out mechanism 63 can be constructed by combining a micromotor 63a with a rack 63b and using the rack 63a as the pushing-out member. Here, the chip elevator 62 and the chip pushing-out mechanism 63 are connected to the controller section 12 as shown in FIG. 11, and receive an operation control from the controller section 12. On the other hand, the stacker 60 itself may have an independent controller section, and the operations of the chip elevator 62 and the chip pushing-out mechanism 63 may be controlled by the controller section on the stacker 60 side.

Furthermore, by providing a holder 39 that stores a plurality of end effectors side by side for exchanging the end effectors 35 of the above-mentioned micromanipulators 30a, 30b, the end effectors 35 can be automatically exchanged in accordance with the needs, so that the analysis work can be carried out continuously and automatically.

Thus, by combining micromanipulators 30a, 30b or an exchanging mechanism for supplying various source materials with the analyzing apparatus 1, the analysis work can be carried out automatically and the required samples can be extracted automatically.

6. MODIFIED EXAMPLES

As shown above, one embodiment of the present invention has been described; however, the present invention is not limited to the contents of the above descriptions alone.

For example, in the above description, a case has been exemplified in which the analysis and manipulations are carried out by hybridization reaction of DNA. However, it is needless to say that this analyzing apparatus can be applied to a case in which analysis and manipulations are carried out utilizing an antibody-antigen reaction, a ligand-receptor reaction, or other biotic or biochemical reactions. In other words, it is sufficient that the samples as an object of analysis and manipulations in the analyzing apparatus is a minute substance.

Further, in the above descriptions, a case has been exemplified in which electrophoresis is utilized as a method for moving solutions or samples such as samples and reagents among the tanks on the analyzing chip 20; however, a different method may be adopted. For example, pressure generated by a micropump may be utilized or a gravity potential may be utilized by varying the height positions of the tanks.

While the invention has been shown and described in detail, the foregoing description is in all aspects illustrative and not restrictive. It is therefore understood that numerous other modifications and variations can be devised without departing from the scope of the invention.

What is claimed is:
1. A microchip comprising:
a channel having at least one internal surface, a substantially trapezoidal-shaped cross-section, and the channel having an upper surface thereof that is longer than a lower surface thereof, wherein an object to be analyzed is capable of traveling through the channel;
an optical element facing the channel to receive light from the object, the optical element having a surface forming a part of the at least one internal surface of the channel; and
a light guide for guiding a light from an external light source to a prescribed area of the channel, a light-emitting surface of the light guide being a portion of a first side surface of the channel, wherein the first side surface of the channel is adapted to concentrate the light emitted from the light guide to the surface of the optical element;
the microchip further comprising, as deflecting elements for approximating the object in the channel to the optical element:
a first electrode provided to face the channel at a vicinity of the optical element, the first electrode provided on the upper surface of the channel; and
a second electrode provided to face the channel at an upstream side of the optical element with respect to a traveling direction of the object, the second electrode provided on the lower surface of the channel,
wherein the optical element is provided at the prescribed area, and
wherein the object is capable of being approximated to the optical element in a direction transverse to a length of the channel by applying a predetermined electric field between the first and second electrodes.
2. A microchip as claimed in claim 1,
wherein the channel further includes a second side surface; and
wherein each of the first and second side surfaces is a sloped surface.
3. A microchip as claimed in claim 2, wherein the light-emitting surface of the light guide is formed to have a slope similar to that of the first side surface of the channel.

* * * * *